United States Patent
Zhang

(10) Patent No.: US 10,656,153 B2
(45) Date of Patent: May 19, 2020

(54) DIAGNOSTIC METHOD AND DEVICES FOR AUTOIMMUNE DISEASE

(71) Applicant: PZM Diagnostics, LLC, Charleston, WV (US)

(72) Inventor: Peilin Zhang, Charleston, WV (US)

(73) Assignee: PZM DIAGNOSTICS, LLC, Charleston, WV (US)

( * ) Notice: Subject to any disclaimer, the term of this patent is extended or adjusted under 35 U.S.C. 154(b) by 0 days.

(21) Appl. No.: 15/903,725

(22) Filed: Feb. 23, 2018

(65) Prior Publication Data

US 2018/0252710 A1 Sep. 6, 2018

Related U.S. Application Data

(60) Provisional application No. 62/462,771, filed on Feb. 23, 2017.

(51) Int. Cl.
- *G01N 33/564* (2006.01)
- *G01N 21/64* (2006.01)
- *G01N 21/76* (2006.01)

(52) U.S. Cl.
CPC .......... *G01N 33/564* (2013.01); *G01N 21/64* (2013.01); *G01N 21/76* (2013.01); *G01N 2021/6441* (2013.01)

(58) Field of Classification Search
CPC .... C07K 14/47; C07K 14/35; C07K 16/1289; C07K 14/205; C07K 14/31; B01F 13/0059; B01F 5/0602; B01L 2300/0681; B01L 2300/0816; B01L 2300/0861; B01L 2300/0867; B01L 3/5027; G01N 2333/9015; G01N 33/68; G01N 33/6812; G01N 33/3818; G01N 2333/245; G01N 2333/35; G01N 2800/12; G01N 33/542; G01N 33/5695; G01N 33/9446; G01N 2333/70514; G01N 2333/70517; G01N 33/505; G01N 33/564; A61K 38/00; A61K 39/00; A61K 2039/543; A61K 2039/552; A61K 2039/55505; A61K 2039/55561; A61K 35/74; A61K 39/018; A61K 39/0208; A61K 39/0233; A61K 39/104; C07H 21/02; C12Q 1/68; C12Q 1/6883; C12Q 1/6886; C12Q 2600/156; C12N 9/0008; C12Y 102/01051; C12Y 102/05001

See application file for complete search history.

(56) References Cited

U.S. PATENT DOCUMENTS 7,759,079 B2 7/2010 Oh
2011/0268744 A1* 11/2011 Garthwaite ............ C07K 14/35
424/158.1

OTHER PUBLICATIONS

Kumar V, Abbas, AK, Aster, JC. Robbins and Cotran Pathologic Basis of Disease—9th edition. 9th Ed. ed: Elsevier; 2015. Cover page and Table of Contents.

Tomkovich S, Jobin C. Microbiota and host immune responses: a love-hate relationship. Immunology. Jan. 2016;147 (1):1-10.

Grigg JB, Sonnenberg GF. Host-Microbiota Interactions Shape Local and Systemic Inflammatory Diseases. J Immunol. Jan. 15, 2017;198(2):564-571.

Valkenburg H, Goslings, WRO, Bots, AW, de Moor, CE, Lorrier, JC. Attack Rates of Streptococcal Pharvngitis, Rheumatic Fever and Glomerulonephritis in the General Population—The Epidemiology of Streptococcal Pharvngitis in One Village during a Two-Year Period. New England Journal of Medicine. 1963;268:694-701.

Kees-Folts D, Abt AB, Domen RE, Freiberg AS. Renal failure after anti-D globulin treatment of idiopathic thrombocytopenic purpura. Pediatr Nephrol. Feb. 2002;17(2):91-96. Abstract only.

Jostins L, Ripke S, Weersma RK, et al. Host-microbe interactions have shaped the genetic architecture of inflammatory bowel disease. Nature. Nov. 1, 2012;491(7422):119-124.

Elkadri AA, Stempak JM, Walters TD, et al. Serum antibodies associated with complex inflammatory bowel disease. Inflamm Bowel Dis. Jun. 2013;19(7):1499-1505. Abstract only.

Pompilio A, De Nicola S, Crocetta V, et al. New insights in *Staphylococcus pseudintermedius* pathogenicity: antibiotic-resistant biofilm formation by a human wound-associated strain. BMC Microbiol. May 21, 2015;15:109.

Somayaji R, Priyantha MA, Rubin JE, Church D. Human infections due to *Staphylococcus pseudintermedius*, an amerging zoonosis of canine origin: report of 24 cases. Diagn Microbiol Infect Dis. Aug. 2016;85(4):471-476. Abstract only.

Kiessling R, Gronberg A, Ivanyi J, et al. Role of hsp60 during autoimmune and bacterial inflammation. Immunol Rev. Jun. 1991;121:91-111.

Campanella C, Marino Gammazza A, Mularoni L, Cappello F, Zummo G, Di Felice V. A comparative analysis of the products of GROEL-1 gene from Chlamydia trachomatis serovar D and the HSP60 var1 transcript from *Homo sapiens* suggests a possible autoimmune response. Int J Immunogenet. Feb. 2009;36(1):73-78. Abstract only.

Dubinsky MC, Lin YC, Dutridge D, et al. Serum immune responses predict rapid disease progression among children with Crohn's disease: immune responses predict disease progression. Am J Gastroenterol. Feb. 2006;101(2):360-3.

Deveraux J., A comprehensive set of sequence analysis programs for the VAX, Nucl. Acids Res. 1984; 12:387-395.

Self and Cook et al., Advances in immunoassay technology, Current Opinion in Biotechnology 1996; 7:60-65. Abstract only.

D. Davies et al., Antibody-antigen complexes, Ann. Rev. Biochem. 1990; 59:439-473. Contents page.

(Continued)

*Primary Examiner* — Sarvamangala Devi
(74) *Attorney, Agent, or Firm* — Andrew D. Wright; Roberts Calderon Safran & Cole, P.C.

(57) ABSTRACT

Devices, solutions and method capable of quantifying a clinically significant amount of antibodies within a plasma sample obtained from an individual by quantifying binding between antibodies within the sample and microbial proteins are disclosed.

6 Claims, 6 Drawing Sheets

Specification includes a Sequence Listing.

(56) References Cited

OTHER PUBLICATIONS

H. Rongen et al., Liposomes and immunoassays, J. Immunol. Methods 1997; 204:105-133. Abstract only.

D. Schmalzing and W. Nashabeh, Capillary electrophoresis based immunoassays: a critical review, Electrophoresis 1997; 18:2184-2193. Abstract only.

Bao, J. et al., Capillary eletrophoretic assays, J. Chromatography B. Biomed. Sci. 1997; 699:463-480. Abstract only.

Antibodies—A Laboratory Manual, E. Harlow and D. Lane, editors, c. 1988 by Cold Spring Harbor Laboratories Press, Cold Spring Harbor, MA ISBN 0-87969-374-6.

Remington's Pharmaceutical Sciences, 16th Ed., A. Oslo editor, c. 1980 by Mack Publishing Co., Easton, PA ISBN 0-912374-02-9.

\* cited by examiner

1. Recombinant RPOB (S. aureus) (amino acid sequence)

```
   1 ........LAG QVVQYGRHRK RRNYARISEV LELPNLIEIQ TKSYEWFLRE GLIEMFRDIS
  61 PIEDFTGNLS LEFVDYRLGE PKYDLEESKN RDATYAAPLR VKVRLIIKET GEVKEQEVFM
 121 GDFPLMTDTG TFVINGAERV IVSQLVRSPS VYFNEKIDKN GRENYDATII PNRGAWLEYE
 181 TDAKDVVYVR IDRTRKLPLT VLLRALGFSS DQEIVDLLGD NEYLRNTLEK DGTENTEQAL
 241 LEIYERLRPG EPPTVENAKS LLYSRFFDPK RYDLASVGRY KTNKKLHLKH RLFNQKLAEP
 301 IVNTETGEIV VEEGTVLDRR KIDEIMDVLE SNANSEVFEL HGSVIDEPVE IQSIKVYVPN
 361 DDEGRTTTVI GNAFPDSEVK CITPADIIAS MSYFFNLLSG IGYTDDIDHL GNRRLRSVGE
 421 LLQNQFRIGL SRMERVVRER MSIQDTESIT PQQLINIRPV IASIKEFFGS SQLSQFMDQA
 481 NPLAELTHKR RLSALGPGGL TRERAQMEVR DVHYSHYGRM CPIETPEGPN IGLINSLSSY
 541 ARVNEFGFIE TPYRKVDLDI HAITDQIDYL TADEEDSYVV AQANSKLDEN GRFMDDEVVC
 601 RFRGNNTVMA KEKMDYMDVS PKQVVSAATA CIPFLENDDS NRALMGANMQ RQAVPLMNPE
 661 APFVGTGMEH VAARDSGAAI TAKHRGRVEH VESNEILVRR LVEENGVEHE GELDRYPLAK
 721 FKRSNSGTCY NQRPIVAVGD VVEYNEILAD GPSMELGEMA LGRNVVVGFM TWDGYNYEDA
 781 VIMSERLVKD DVYTSIHIEE YESEARDTKL GPEEITRDIP NVSESALKNL DDRGIVYIGA
 841 EVKDGDILVG KVTPKGVTEL TAEERLLHAI FGEKAREVRD TSLRVPHGAG GIVLDVKVFN
 901 REEGDDTLSP GVNQLVRVYI VQKRKIHVGD KMCGRHGNKG VISKIVPEED MPYLPDGRPI
 961 DIMLNPLGVP SRMNIGQVLE LHLGMAAKNL GIHVASPVFD GANDDDVWST IEEAGMARDG
1021 KTVLYDGRTG EPFDNRISVG VMYMLKLAHM VDDKLHARST GPYSLVTQQP LGGKAQFGGQ
1081 RFGEMEVWAL EAYGAAYTLQ EILTYKSDDT VGRVKTYEAI VKGENISRPS VPESFRVLMK
1141 ELQSLGLDVK VMDEQDNEIE MTDVDDDDVV ERKVDLQQND APETQKEVTD
```

2. Recombinant Elongation factor G (EF-G, from S. aureus)

```
   1 ........MAR EFSLEKTRNI GIMAHIDAGK TTTTERILYY TGRIHKIGET HEGASQMDWM
  61 EQEQDRGITI TSAATTAAWE GHRVNIIDTP GHVDFTVEVE RSLRVLDGAV TVLDAQSGVE
 121 PQTETVWRQA TTYGVPRIVF VNKMDKLGAN FEYSVSTLHD RLQANAAPIQ LPIGAEDEFE
 181 AIIDLVEMKC FKYTNDLGTE IEEIEIPEDH LDRAEEARAS LIEAVAETSD ELMEKYLGDE
 241 EISVSELKEA IRQATTNVEF YPVLCGTAFK NKGVQLMLDA VIDYLPSPLD VKPIIGHRAS
 301 NPEEEVIAKA DDSAEFAALA FKVMTDPYVG KLTFFRVYSG TMTSGSYVKN STKGKRERVG
 361 RLLQMHANSR QEIDTVYSGD IAAAVGLKDT GTGDTLCGEK NDIILESMEF PEPVIHLSVE
 421 PKSKADQDKM TQALVKLQEE DPTFHAHTDE ETGQVIIGGM GELHLDILVD RMKKEFNVEC
 481 NVGAPMVSYR ETFKSSAQVQ GKFSRQSGGR GQYGDVHIEF TPNETGAGFE FENAIVGGVV
 541 PREYIPSVEA GLKDAMENGV LAGYPLIDVK AKLYDGSYHD VDSSEMAFKI AASLALKEAA
 601 KKCDPVILEP MMKVTIEMPE EYMGDIMGDV TSRRGRVDGM EPRGNAQVVN AYVPLSEMFG
 661 YATSLRSNTQ GRGTYTMYFD HYAEVPKSIA EDHKKNKGE
```

Figure 6

3. Recombinant heat shock protein 65 (hsp65 from M. tuberculosis)

```
1   :::::::MAK TIAYDEEARR GLERGLNALA DAVKVTLGPK GRNVVLEKKW GAPTITNDGV
61  SIAKEIELED PYEKIGAELV KEVAKKTDDV AGDGTTTATV LAQALVREGL RNVAAGANPL
121 GLKRGIEKAV EKVTETLLKG AKEVETKEQI AATAAISAGD QSIGDLIAEA MDKVGNEGVI
181 TVEESNTFGL QLELTEGMRF DKGYISGYFV TDPERQEAVL EDPYILLVSS KVSTVKDLLP
241 LLEKVIGAGK PLLIIAEDVE GEALSTLVVN KIRGTFKSVA VKAPGFGDRR KAMLQDMAIL
301 TGGQVISEEV GLTLENADLS LLGKARKVVV TKDETTIVEG AGDTDAIAGR VAQIRQEIEN
361 SDSDYDREKL QERLAKLAGG VAVIKAGAAT EVELKERKHR IEDAVRNAKA AVEEGIVAGG
421 GVTLLQAAPT LDELKLEGDE ATGANIVKVA LEAPLKQIAF NSGLEPGVVA EKVRNLPAGH
481 GLNAQTGVYE DLLAAGVADP VKVTRSALQN AASIAGLFLT TEAVVADKPE KEKASVPGGG
541 DMGGMDF
```

4. Recombinant ATP synthase alpha (ATP5a from S. aureus)

```
1   :::::::MAI KAEEISALLR SQIENYESEM SVTDVGTVLQ IGDGIALIHG LNDVMAGELV
61  EFHNGVLGLA QNLEESNVGV VILGPYTGIT EGDEVKRTGR IMEVPVGEEL IGRVVNPLGQ
121 PIDGQGPINT TKTRPVEKKA TGVMDRKSVD EPLQTGIKAI DALVPIGRGQ RELIIGDRQT
181 GKTTIAIDTI LNQKDQGTIC IYVAIGQKDS TVRANVEKLR QAGALDYTIV VAASASEPSP
241 LLYIAPYSGV TMGEEFMFNG KHVLIVYDDL TKQAAAYREL SLLLRRPPGR EAYPGDVFYL
301 HSRLLERAAK LNDDLGGGSI TALPIIETQA GDISAYVPTN VISITDGQIF LQSDLFFSGV
361 RPAINAGQSV SRVGGSAQIK AMRKVAGTLR LDLASYRELE SFAQFGSDLD EFTASKLERG
421 KRTVEVLKQD QNKPLPVEHQ VLIIYALTKG YLDDIPVVDI TRFEDELNHW AESNATELLN
481 EIRETGGLPD AEKFDTAINE FKKSFSKSE
```

5. Recombinant elongation factor Tu (EF-Tu from E. coli)

```
1   :::::::MSK EKFERTKPHV NVGTIGHVDH GKTTLTAAIT TVLAKTYGGA ARAFDQIDNA
61  PEEKARGITI NTSHVEYDTP TRHYAHVDCP GHADYVKNMI TGAAQMDGAI LVVAATDGPM
121 PQTREHILLG RQVGVPYIIV FLNKCDMVDD EELLELVEME VRELLSQYDF PGDDTPIVRG
181 SALKALEGDA EWEAKILELA GFLDSYIPEP ERAIDKPFLL PIEDVFSISG RGTVVTGRVE
241 RGIIKVGEEV EIVGIKETQK STCTGVEMFR KLLDEGRAGE NVGVLLRGIK REEIERGQVL
301 AKPGTIKPHT KFESEVYILS KDEGGRHTPF FKGYRPQFYF RTTDVTGTIE LPEGVEMVMP
361 GDNIKMVVTL IHPIAMDDGL RFAIREGGRT VGAGVVAKVL S
```

6. Recombinant outer membrane porin protein C (nmpC from E.coli)

```
1   :::::::AEI YNKDSNKLDL YGKVNAKHYF SSNDADDGDT TYARLGFKGE TQINDQLTGF
61  GQWEYEFKGN RAESQGSSKD KTRLAFAGLK FGDYGSIDYG RNYGVAYDIG AWTDVLPEFG
121 GDTWTQTDVF MTQRATGVAT YRNNDFFGLV DGLNFAAQYQ GKNDRSDFDN YTEGNGDGFG
181 FSATYEYEGF GIGATYAKSD RTDTQVNAGK VLPEVFASGK NAEVWAAGLK YDANNIYLAT
241 TYSETQNMTV FADHFVANKA QNFEAVAQYQ FDFGLRPSVA YLQSKGKDLG VWGDQDLVKY
301 VDVGATYYFN KNMSTFVDYK INLLDKNDFT KALGVSTDDI VAVGLVYQF
```

Figure 7

SEQUENCE LISTING

```
<160> NUMBER OF SEQ ID NOS: 6

<210> SEQ ID NO 1
<211> LENGTH: 1190
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 1

```
Met His His His His His Leu Ala Gly Gln Val Gln Tyr Gly
1               5                   10                  15

Arg His Arg Lys Arg Arg Asn Tyr Ala Arg Ile Ser Glu Val Leu Glu
                20                  25                  30

Leu Pro Asn Leu Ile Glu Ile Gln Thr Lys Ser Tyr Glu Trp Phe Leu
            35                  40                  45

Arg Glu Gly Leu Ile Glu Met Phe Arg Asp Ile Ser Pro Ile Glu Asp
        50                  55                  60

Phe Thr Gly Asn Leu Ser Leu Glu Phe Val Asp Tyr Arg Leu Gly Glu
65                  70                  75                  80

Pro Lys Tyr Asp Leu Glu Glu Ser Lys Asn Arg Asp Ala Thr Tyr Ala
                85                  90                  95

Ala Pro Leu Arg Val Lys Val Arg Leu Ile Ile Lys Glu Thr Gly Glu
            100                 105                 110

Val Lys Glu Gln Glu Val Phe Met Gly Asp Phe Pro Leu Met Thr Asp
        115                 120                 125

Thr Gly Thr Phe Val Ile Asn Gly Ala Glu Arg Val Ile Val Ser Gln
130                 135                 140

Leu Val Arg Ser Pro Ser Val Tyr Phe Asn Glu Lys Ile Asp Lys Asn
145                 150                 155                 160

Gly Arg Glu Asn Tyr Asp Ala Thr Ile Ile Pro Asn Arg Gly Ala Trp
                165                 170                 175

Leu Glu Tyr Glu Thr Asp Ala Lys Asp Val Val Tyr Val Arg Ile Asp
            180                 185                 190

Arg Thr Arg Lys Leu Pro Leu Thr Val Leu Leu Arg Ala Leu Gly Phe
        195                 200                 205

Ser Ser Asp Gln Glu Ile Val Asp Leu Leu Gly Asp Asn Glu Tyr Leu
210                 215                 220

Arg Asn Thr Leu Glu Lys Asp Gly Thr Glu Asn Thr Glu Gln Ala Leu
225                 230                 235                 240

Leu Glu Ile Tyr Glu Arg Leu Arg Pro Gly Glu Pro Thr Val Glu
            245                 250                 255

Asn Ala Lys Ser Leu Leu Tyr Ser Arg Phe Phe Asp Pro Lys Arg Tyr
        260                 265                 270

Asp Leu Ala Ser Val Gly Arg Tyr Lys Thr Asn Lys Lys Leu His Leu
    275                 280                 285

Lys His Arg Leu Phe Asn Gln Lys Leu Ala Glu Pro Ile Val Asn Thr
290                 295                 300

Glu Thr Gly Glu Ile Val Glu Glu Gly Thr Val Leu Asp Arg Arg
305                 310                 315                 320

Lys Ile Asp Glu Ile Met Asp Val Leu Glu Ser Asn Ala Asn Ser Glu
            325                 330                 335

Val Phe Glu Leu His Gly Ser Val Ile Asp Glu Pro Val Glu Ile Gln
        340                 345                 350

Ser Ile Lys Val Tyr Val Pro Asn Asp Glu Gly Arg Thr Thr Thr
    355                 360                 365

Val Ile Gly Asn Ala Phe Pro Asp Ser Glu Val Lys Cys Ile Thr Pro
370                 375                 380

Ala Asp Ile Ile Ala Ser Met Ser Tyr Phe Phe Asn Leu Leu Ser Gly
385                 390                 395                 400
```

-continued

Ile Gly Tyr Thr Asp Asp Ile Asp His Leu Gly Asn Arg Arg Leu Arg
            405                 410                 415

Ser Val Gly Glu Leu Leu Gln Asn Gln Phe Arg Ile Gly Leu Ser Arg
        420                 425                 430

Met Glu Arg Val Val Arg Glu Arg Met Ser Ile Gln Asp Thr Glu Ser
        435                 440                 445

Ile Thr Pro Gln Gln Leu Ile Asn Ile Arg Pro Val Ile Ala Ser Ile
    450                 455                 460

Lys Glu Phe Phe Gly Ser Ser Gln Leu Ser Gln Phe Met Asp Gln Ala
465                 470                 475                 480

Asn Pro Leu Ala Glu Leu Thr His Lys Arg Arg Leu Ser Ala Leu Gly
                485                 490                 495

Pro Gly Gly Leu Thr Arg Glu Arg Ala Gln Met Glu Val Arg Asp Val
            500                 505                 510

His Tyr Ser His Tyr Gly Arg Met Cys Pro Ile Glu Thr Pro Glu Gly
        515                 520                 525

Pro Asn Ile Gly Leu Ile Asn Ser Leu Ser Ser Tyr Ala Arg Val Asn
        530                 535                 540

Glu Phe Gly Phe Ile Glu Thr Pro Tyr Arg Lys Val Asp Leu Asp Ile
545                 550                 555                 560

His Ala Ile Thr Asp Gln Ile Asp Tyr Leu Thr Ala Asp Glu Glu Asp
                565                 570                 575

Ser Tyr Val Val Ala Gln Ala Asn Ser Lys Leu Asp Glu Asn Gly Arg
            580                 585                 590

Phe Met Asp Asp Glu Val Val Cys Arg Phe Arg Gly Asn Asn Thr Val
        595                 600                 605

Met Ala Lys Glu Lys Met Asp Tyr Met Asp Val Ser Pro Lys Gln Val
        610                 615                 620

Val Ser Ala Ala Thr Ala Cys Ile Pro Phe Leu Glu Asn Asp Asp Ser
625                 630                 635                 640

Asn Arg Ala Leu Met Gly Ala Asn Met Gln Arg Gln Ala Val Pro Leu
                645                 650                 655

Met Asn Pro Glu Ala Pro Phe Val Gly Thr Gly Met Glu His Val Ala
            660                 665                 670

Ala Arg Asp Ser Gly Ala Ala Ile Thr Ala Lys His Arg Gly Arg Val
        675                 680                 685

Glu His Val Glu Ser Asn Glu Ile Leu Val Arg Arg Leu Val Glu Glu
        690                 695                 700

Asn Gly Val Glu His Glu Gly Glu Leu Asp Arg Tyr Pro Leu Ala Lys
705                 710                 715                 720

Phe Lys Arg Ser Asn Ser Gly Thr Cys Tyr Asn Gln Arg Pro Ile Val
                725                 730                 735

Ala Val Gly Asp Val Val Glu Tyr Asn Glu Ile Leu Ala Asp Gly Pro
            740                 745                 750

Ser Met Glu Leu Gly Glu Met Ala Leu Gly Arg Asn Val Val Val Gly
        755                 760                 765

Phe Met Thr Trp Asp Gly Tyr Asn Tyr Glu Asp Ala Val Ile Met Ser
        770                 775                 780

Glu Arg Leu Val Lys Asp Asp Val Tyr Thr Ser Ile His Ile Glu Glu
785                 790                 795                 800

Tyr Glu Ser Glu Ala Arg Asp Thr Lys Leu Gly Pro Glu Glu Ile Thr
                805                 810                 815

```
Arg Asp Ile Pro Asn Val Ser Glu Ser Ala Leu Lys Asn Leu Asp Asp
                820                 825                 830

Arg Gly Ile Val Tyr Ile Gly Ala Glu Val Lys Asp Gly Asp Ile Leu
            835                 840                 845

Val Gly Lys Val Thr Pro Lys Gly Val Thr Glu Leu Thr Ala Glu Glu
        850                 855                 860

Arg Leu Leu His Ala Ile Phe Gly Glu Lys Ala Arg Glu Val Arg Asp
865                 870                 875                 880

Thr Ser Leu Arg Val Pro His Gly Ala Gly Ile Val Leu Asp Val
                885                 890                 895

Lys Val Phe Asn Arg Glu Glu Gly Asp Asp Thr Leu Ser Pro Gly Val
                900                 905                 910

Asn Gln Leu Val Arg Val Tyr Ile Val Gln Lys Arg Lys Ile His Val
                915                 920                 925

Gly Asp Lys Met Cys Gly Arg His Gly Asn Lys Gly Val Ile Ser Lys
            930                 935                 940

Ile Val Pro Glu Glu Asp Met Pro Tyr Leu Pro Asp Gly Arg Pro Ile
945                 950                 955                 960

Asp Ile Met Leu Asn Pro Leu Gly Val Pro Ser Arg Met Asn Ile Gly
                965                 970                 975

Gln Val Leu Glu Leu His Leu Gly Met Ala Ala Lys Asn Leu Gly Ile
                980                 985                 990

His Val Ala Ser Pro Val Phe Asp Gly Ala Asn Asp Asp Val Trp
            995                 1000                1005

Ser Thr Ile Glu Glu Ala Gly Met Ala Arg Asp Gly Lys Thr Val
    1010                1015                1020

Leu Tyr Asp Gly Arg Thr Gly Glu Pro Phe Asp Asn Arg Ile Ser
    1025                1030                1035

Val Gly Val Met Tyr Met Leu Lys Leu Ala His Met Val Asp Asp
    1040                1045                1050

Lys Leu His Ala Arg Ser Thr Gly Pro Tyr Ser Leu Val Thr Gln
    1055                1060                1065

Gln Pro Leu Gly Gly Lys Ala Gln Phe Gly Gly Gln Arg Phe Gly
    1070                1075                1080

Glu Met Glu Val Trp Ala Leu Glu Ala Tyr Gly Ala Ala Tyr Thr
    1085                1090                1095

Leu Gln Glu Ile Leu Thr Tyr Lys Ser Asp Asp Thr Val Gly Arg
    1100                1105                1110

Val Lys Thr Tyr Glu Ala Ile Val Lys Gly Glu Asn Ile Ser Arg
    1115                1120                1125

Pro Ser Val Pro Glu Ser Phe Arg Val Leu Met Lys Glu Leu Gln
    1130                1135                1140

Ser Leu Gly Leu Asp Val Lys Val Met Asp Glu Gln Asp Asn Glu
    1145                1150                1155

Ile Glu Met Thr Asp Val Asp Asp Asp Val Val Glu Arg Lys
    1160                1165                1170

Val Asp Leu Gln Gln Asn Asp Ala Pro Glu Thr Gln Lys Glu Val
    1175                1180                1185

Thr Asp
    1190

<210> SEQ ID NO 2
<211> LENGTH: 700
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 2

```
Met His His His His His Met Ala Arg Glu Phe Ser Leu Glu Lys
1               5                   10                  15

Thr Arg Asn Ile Gly Ile Met Ala His Ile Asp Ala Gly Lys Thr Thr
            20                  25                  30

Thr Thr Glu Arg Ile Leu Tyr Tyr Thr Gly Arg Ile His Lys Ile Gly
        35                  40                  45

Glu Thr His Glu Gly Ala Ser Gln Met Asp Trp Met Glu Gln Glu Gln
    50                  55                  60

Asp Arg Gly Ile Thr Ile Thr Ser Ala Ala Thr Thr Ala Ala Trp Glu
65                  70                  75                  80

Gly His Arg Val Asn Ile Ile Asp Thr Pro Gly His Val Asp Phe Thr
                85                  90                  95

Val Glu Val Glu Arg Ser Leu Arg Val Leu Asp Gly Ala Val Thr Val
            100                 105                 110

Leu Asp Ala Gln Ser Gly Val Glu Pro Gln Thr Glu Thr Val Trp Arg
        115                 120                 125

Gln Ala Thr Thr Tyr Gly Val Pro Arg Ile Val Phe Val Asn Lys Met
130                 135                 140

Asp Lys Leu Gly Ala Asn Phe Glu Tyr Ser Val Ser Thr Leu His Asp
145                 150                 155                 160

Arg Leu Gln Ala Asn Ala Ala Pro Ile Gln Leu Pro Ile Gly Ala Glu
                165                 170                 175

Asp Glu Phe Glu Ala Ile Ile Asp Leu Val Glu Met Lys Cys Phe Lys
            180                 185                 190

Tyr Thr Asn Asp Leu Gly Thr Glu Ile Glu Glu Ile Glu Ile Pro Glu
        195                 200                 205

Asp His Leu Asp Arg Ala Glu Glu Ala Arg Ala Ser Leu Ile Glu Ala
210                 215                 220

Val Ala Glu Thr Ser Asp Glu Leu Met Glu Lys Tyr Leu Gly Asp Glu
225                 230                 235                 240

Glu Ile Ser Val Ser Glu Leu Lys Glu Ala Ile Arg Gln Ala Thr Thr
                245                 250                 255

Asn Val Glu Phe Tyr Pro Val Leu Cys Gly Thr Ala Phe Lys Asn Lys
            260                 265                 270

Gly Val Gln Leu Met Leu Asp Ala Val Ile Asp Tyr Leu Pro Ser Pro
        275                 280                 285

Leu Asp Val Lys Pro Ile Ile Gly His Arg Ala Ser Asn Pro Glu Glu
290                 295                 300

Glu Val Ile Ala Lys Ala Asp Asp Ser Ala Glu Phe Ala Ala Leu Ala
305                 310                 315                 320

Phe Lys Val Met Thr Asp Pro Tyr Val Gly Lys Leu Thr Phe Phe Arg
                325                 330                 335

Val Tyr Ser Gly Thr Met Thr Ser Gly Ser Tyr Val Lys Asn Ser Thr
            340                 345                 350

Lys Gly Lys Arg Glu Arg Val Gly Arg Leu Leu Gln Met His Ala Asn
        355                 360                 365

Ser Arg Gln Glu Ile Asp Thr Val Tyr Ser Gly Asp Ile Ala Ala Ala
370                 375                 380
```

Val Gly Leu Lys Asp Thr Gly Thr Gly Asp Thr Leu Cys Gly Glu Lys
385                 390                 395                 400

Asn Asp Ile Ile Leu Glu Ser Met Glu Phe Pro Glu Pro Val Ile His
            405                 410                 415

Leu Ser Val Glu Pro Lys Ser Lys Ala Asp Gln Asp Lys Met Thr Gln
        420                 425                 430

Ala Leu Val Lys Leu Gln Glu Glu Asp Pro Thr Phe His Ala His Thr
            435                 440                 445

Asp Glu Glu Thr Gly Gln Val Ile Ile Gly Gly Met Gly Glu Leu His
450                 455                 460

Leu Asp Ile Leu Val Asp Arg Met Lys Lys Glu Phe Asn Val Glu Cys
465                 470                 475                 480

Asn Val Gly Ala Pro Met Val Ser Tyr Arg Glu Thr Phe Lys Ser Ser
                485                 490                 495

Ala Gln Val Gln Gly Lys Phe Ser Arg Gln Ser Gly Arg Gly Gln
                500                 505                 510

Tyr Gly Asp Val His Ile Glu Phe Thr Pro Asn Glu Thr Gly Ala Gly
            515                 520                 525

Phe Glu Phe Glu Asn Ala Ile Val Gly Gly Val Val Pro Arg Glu Tyr
530                 535                 540

Ile Pro Ser Val Glu Ala Gly Leu Lys Asp Ala Met Glu Asn Gly Val
545                 550                 555                 560

Leu Ala Gly Tyr Pro Leu Ile Asp Val Lys Ala Lys Leu Tyr Asp Gly
                565                 570                 575

Ser Tyr His Asp Val Asp Ser Ser Glu Met Ala Phe Lys Ile Ala Ala
            580                 585                 590

Ser Leu Ala Leu Lys Glu Ala Ala Lys Lys Cys Asp Pro Val Ile Leu
            595                 600                 605

Glu Pro Met Met Lys Val Thr Ile Glu Met Pro Glu Glu Tyr Met Gly
        610                 615                 620

Asp Ile Met Gly Asp Val Thr Ser Arg Arg Gly Arg Val Asp Gly Met
625                 630                 635                 640

Glu Pro Arg Gly Asn Ala Gln Val Val Asn Ala Tyr Val Pro Leu Ser
                645                 650                 655

Glu Met Phe Gly Tyr Ala Thr Ser Leu Arg Ser Asn Thr Gln Gly Arg
            660                 665                 670

Gly Thr Tyr Thr Met Tyr Phe Asp His Tyr Ala Glu Val Pro Lys Ser
        675                 680                 685

Ile Ala Glu Asp Ile Ile Lys Lys Asn Lys Gly Glu
690                 695                 700

<210> SEQ ID NO 3
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met His His His His His Met Ala Lys Thr Ile Ala Tyr Asp Glu
1               5                   10                  15

Glu Ala Arg Arg Gly Leu Glu Arg Gly Leu Asn Ala Leu Ala Asp Ala
            20                  25                  30

Val Lys Val Thr Leu Gly Pro Lys Gly Arg Asn Val Val Leu Glu Lys
        35                  40                  45

```
Lys Trp Gly Ala Pro Thr Ile Thr Asn Asp Gly Val Ser Ile Ala Lys
 50                  55                  60

Glu Ile Glu Leu Glu Asp Pro Tyr Glu Lys Ile Gly Ala Glu Leu Val
 65                  70                  75                  80

Lys Glu Val Ala Lys Lys Thr Asp Asp Val Ala Gly Asp Gly Thr Thr
                 85                  90                  95

Thr Ala Thr Val Leu Ala Gln Ala Leu Val Arg Glu Gly Leu Arg Asn
                100                 105                 110

Val Ala Ala Gly Ala Asn Pro Leu Gly Leu Lys Arg Gly Ile Glu Lys
                115                 120                 125

Ala Val Glu Lys Val Thr Glu Thr Leu Leu Lys Gly Ala Lys Glu Val
                130                 135                 140

Glu Thr Lys Glu Gln Ile Ala Ala Thr Ala Ala Ile Ser Ala Gly Asp
145                 150                 155                 160

Gln Ser Ile Gly Asp Leu Ile Ala Glu Ala Met Asp Lys Val Gly Asn
                165                 170                 175

Glu Gly Val Ile Thr Val Glu Glu Ser Asn Thr Phe Gly Leu Gln Leu
                180                 185                 190

Glu Leu Thr Glu Gly Met Arg Phe Asp Lys Gly Tyr Ile Ser Gly Tyr
                195                 200                 205

Phe Val Thr Asp Pro Glu Arg Gln Glu Ala Val Leu Glu Asp Pro Tyr
                210                 215                 220

Ile Leu Leu Val Ser Ser Lys Val Ser Thr Val Lys Asp Leu Leu Pro
225                 230                 235                 240

Leu Leu Glu Lys Val Ile Gly Ala Gly Lys Pro Leu Leu Ile Ile Ala
                245                 250                 255

Glu Asp Val Glu Gly Glu Ala Leu Ser Thr Leu Val Val Asn Lys Ile
                260                 265                 270

Arg Gly Thr Phe Lys Ser Val Ala Val Lys Ala Pro Gly Phe Gly Asp
                275                 280                 285

Arg Arg Lys Ala Met Leu Gln Asp Met Ala Ile Leu Thr Gly Gly Gln
                290                 295                 300

Val Ile Ser Glu Glu Val Gly Leu Thr Leu Glu Asn Ala Asp Leu Ser
305                 310                 315                 320

Leu Leu Gly Lys Ala Arg Lys Val Val Thr Lys Asp Glu Thr Thr
                325                 330                 335

Ile Val Glu Gly Ala Gly Asp Thr Asp Ala Ile Ala Gly Arg Val Ala
                340                 345                 350

Gln Ile Arg Gln Glu Ile Glu Asn Ser Asp Ser Asp Tyr Asp Arg Glu
                355                 360                 365

Lys Leu Gln Glu Arg Leu Ala Lys Leu Ala Gly Gly Val Ala Val Ile
                370                 375                 380

Lys Ala Gly Ala Ala Thr Glu Val Glu Leu Lys Glu Arg Lys His Arg
385                 390                 395                 400

Ile Glu Asp Ala Val Arg Asn Ala Lys Ala Ala Val Glu Glu Gly Ile
                405                 410                 415

Val Ala Gly Gly Gly Val Thr Leu Leu Gln Ala Ala Pro Thr Leu Asp
                420                 425                 430

Glu Leu Lys Leu Glu Gly Asp Glu Ala Thr Gly Ala Asn Ile Val Lys
                435                 440                 445

Val Ala Leu Glu Ala Pro Leu Lys Gln Ile Ala Phe Asn Ser Gly Leu
450                 455                 460
```

```
Glu Pro Gly Val Val Ala Glu Lys Val Arg Asn Leu Pro Ala Gly His
465                 470                 475                 480

Gly Leu Asn Ala Gln Thr Gly Val Tyr Glu Asp Leu Leu Ala Ala Gly
            485                 490                 495

Val Ala Asp Pro Val Lys Val Thr Arg Ser Ala Leu Gln Asn Ala Ala
            500                 505                 510

Ser Ile Ala Gly Leu Phe Leu Thr Thr Glu Ala Val Val Ala Asp Lys
            515                 520                 525

Pro Glu Lys Glu Lys Ala Ser Val Pro Gly Gly Asp Met Gly Gly
    530                 535                 540

Met Asp Phe
545

<210> SEQ ID NO 4
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met His His His His His Met Ala Ile Lys Ala Glu Glu Ile Ser
1               5                   10                  15

Ala Leu Leu Arg Ser Gln Ile Glu Asn Tyr Glu Ser Glu Met Ser Val
            20                  25                  30

Thr Asp Val Gly Thr Val Leu Gln Ile Gly Asp Gly Ile Ala Leu Ile
            35                  40                  45

His Gly Leu Asn Asp Val Met Ala Gly Glu Leu Val Glu Phe His Asn
        50                  55                  60

Gly Val Leu Gly Leu Ala Gln Asn Leu Glu Ser Asn Val Gly Val
65                  70                  75                  80

Val Ile Leu Gly Pro Tyr Thr Gly Ile Thr Glu Gly Asp Glu Val Lys
                85                  90                  95

Arg Thr Gly Arg Ile Met Glu Val Pro Val Gly Glu Glu Leu Ile Gly
            100                 105                 110

Arg Val Val Asn Pro Leu Gly Gln Pro Ile Asp Gly Gln Gly Pro Ile
            115                 120                 125

Asn Thr Thr Lys Thr Arg Pro Val Glu Lys Lys Ala Thr Gly Val Met
    130                 135                 140

Asp Arg Lys Ser Val Asp Glu Pro Leu Gln Thr Gly Ile Lys Ala Ile
145                 150                 155                 160

Asp Ala Leu Val Pro Ile Gly Arg Gly Gln Arg Glu Leu Ile Ile Gly
                165                 170                 175

Asp Arg Gln Thr Gly Lys Thr Thr Ile Ala Ile Asp Thr Ile Leu Asn
            180                 185                 190

Gln Lys Asp Gln Gly Thr Ile Cys Ile Tyr Val Ala Ile Gly Gln Lys
        195                 200                 205

Asp Ser Thr Val Arg Ala Asn Val Glu Lys Leu Arg Gln Ala Gly Ala
    210                 215                 220

Leu Asp Tyr Thr Ile Val Val Ala Ala Ser Ala Ser Glu Pro Ser Pro
225                 230                 235                 240

Leu Leu Tyr Ile Ala Pro Tyr Ser Gly Val Thr Met Gly Glu Glu Phe
                245                 250                 255

Met Phe Asn Gly Lys His Val Leu Ile Val Tyr Asp Asp Leu Thr Lys
            260                 265                 270
```

```
Gln Ala Ala Ala Tyr Arg Glu Leu Ser Leu Leu Arg Arg Pro Pro
            275                 280                 285

Gly Arg Glu Ala Tyr Pro Gly Asp Val Phe Tyr Leu His Ser Arg Leu
290                 295                 300

Leu Glu Arg Ala Ala Lys Leu Asn Asp Asp Leu Gly Gly Gly Ser Ile
305                 310                 315                 320

Thr Ala Leu Pro Ile Ile Glu Thr Gln Ala Gly Asp Ile Ser Ala Tyr
                325                 330                 335

Val Pro Thr Asn Val Ile Ser Ile Thr Asp Gly Gln Ile Phe Leu Gln
                340                 345                 350

Ser Asp Leu Phe Phe Ser Gly Val Arg Pro Ala Ile Asn Ala Gly Gln
            355                 360                 365

Ser Val Ser Arg Val Gly Gly Ser Ala Gln Ile Lys Ala Met Lys Lys
        370                 375                 380

Val Ala Gly Thr Leu Arg Leu Asp Leu Ala Ser Tyr Arg Glu Leu Glu
385                 390                 395                 400

Ser Phe Ala Gln Phe Gly Ser Asp Leu Asp Glu Phe Thr Ala Ser Lys
                405                 410                 415

Leu Glu Arg Gly Lys Arg Thr Val Glu Val Leu Lys Gln Asp Gln Asn
            420                 425                 430

Lys Pro Leu Pro Val Glu His Gln Val Leu Ile Ile Tyr Ala Leu Thr
        435                 440                 445

Lys Gly Tyr Leu Asp Asp Ile Pro Val Val Asp Ile Thr Arg Phe Glu
    450                 455                 460

Asp Glu Leu Asn His Trp Ala Glu Ser Asn Ala Thr Glu Leu Leu Asn
465                 470                 475                 480

Glu Ile Arg Glu Thr Gly Gly Leu Pro Asp Ala Glu Lys Phe Asp Thr
                485                 490                 495

Ala Ile Asn Glu Phe Lys Lys Ser Phe Ser Lys Ser Glu
                500                 505

<210> SEQ ID NO 5
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met His His His His His Met Ser Lys Glu Lys Phe Glu Arg Thr
1               5                   10                  15

Lys Pro His Val Asn Val Gly Thr Ile Gly His Val Asp His Gly Lys
                20                  25                  30

Thr Thr Leu Thr Ala Ala Ile Thr Thr Val Leu Ala Lys Thr Tyr Gly
            35                  40                  45

Gly Ala Ala Arg Ala Phe Asp Gln Ile Asp Asn Ala Pro Glu Glu Lys
        50                  55                  60

Ala Arg Gly Ile Thr Ile Asn Thr Ser His Val Glu Tyr Asp Thr Pro
65                  70                  75                  80

Thr Arg His Tyr Ala His Val Asp Cys Pro Gly His Ala Asp Tyr Val
                85                  90                  95

Lys Asn Met Ile Thr Gly Ala Ala Gln Met Asp Gly Ala Ile Leu Val
                100                 105                 110

Val Ala Ala Thr Asp Gly Pro Met Pro Gln Thr Arg Glu His Ile Leu
```

```
                115                 120                 125
Leu Gly Arg Gln Val Gly Val Pro Tyr Ile Ile Val Phe Leu Asn Lys
            130                 135                 140

Cys Asp Met Val Asp Asp Glu Glu Leu Leu Glu Leu Val Glu Met Glu
145                 150                 155                 160

Val Arg Glu Leu Leu Ser Gln Tyr Asp Phe Pro Gly Asp Asp Thr Pro
                165                 170                 175

Ile Val Arg Gly Ser Ala Leu Lys Ala Leu Glu Gly Asp Ala Glu Trp
            180                 185                 190

Glu Ala Lys Ile Leu Glu Leu Ala Gly Phe Leu Asp Ser Tyr Ile Pro
                195                 200                 205

Glu Pro Glu Arg Ala Ile Asp Lys Pro Phe Leu Leu Pro Ile Glu Asp
            210                 215                 220

Val Phe Ser Ile Ser Gly Arg Gly Thr Val Thr Gly Arg Val Glu
225                 230                 235                 240

Arg Gly Ile Ile Lys Val Gly Glu Glu Val Glu Ile Val Gly Ile Lys
                245                 250                 255

Glu Thr Gln Lys Ser Thr Cys Thr Gly Val Glu Met Phe Arg Lys Leu
            260                 265                 270

Leu Asp Glu Gly Arg Ala Gly Glu Asn Val Gly Val Leu Leu Arg Gly
            275                 280                 285

Ile Lys Arg Glu Glu Ile Glu Arg Gly Gln Val Leu Ala Lys Pro Gly
            290                 295                 300

Thr Ile Lys Pro His Thr Lys Phe Glu Ser Glu Val Tyr Ile Leu Ser
305                 310                 315                 320

Lys Asp Glu Gly Gly Arg His Thr Pro Phe Phe Lys Gly Tyr Arg Pro
                325                 330                 335

Gln Phe Tyr Phe Arg Thr Thr Asp Val Thr Gly Thr Ile Glu Leu Pro
            340                 345                 350

Glu Gly Val Glu Met Val Met Pro Gly Asp Asn Ile Lys Met Val Val
            355                 360                 365

Thr Leu Ile His Pro Ile Ala Met Asp Asp Gly Leu Arg Phe Ala Ile
        370                 375                 380

Arg Glu Gly Gly Arg Thr Val Gly Ala Gly Val Val Ala Lys Val Leu
385                 390                 395                 400

Ser

<210> SEQ ID NO 6
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met His His His His His Ala Glu Ile Tyr Asn Lys Asp Ser Asn
1               5                   10                  15

Lys Leu Asp Leu Tyr Gly Lys Val Asn Ala Lys His Tyr Phe Ser Ser
            20                  25                  30

Asn Asp Ala Asp Asp Gly Asp Thr Thr Tyr Ala Arg Leu Gly Phe Lys
        35                  40                  45

Gly Glu Thr Gln Ile Asn Asp Gln Leu Thr Gly Phe Gly Gln Trp Glu
    50                  55                  60

Tyr Glu Phe Lys Gly Asn Arg Ala Glu Ser Gln Gly Ser Ser Lys Asp
```

-continued

```
            65                  70                  75                  80
Lys Thr Arg Leu Ala Phe Ala Gly Leu Lys Phe Gly Asp Tyr Gly Ser
                85                  90                  95
Ile Asp Tyr Gly Arg Asn Tyr Gly Val Ala Tyr Asp Ile Gly Ala Trp
               100                 105                 110
Thr Asp Val Leu Pro Glu Phe Gly Gly Asp Thr Trp Thr Gln Thr Asp
           115                 120                 125
Val Phe Met Thr Gln Arg Ala Thr Gly Val Ala Thr Tyr Arg Asn Asn
        130                 135                 140
Asp Phe Phe Gly Leu Val Asp Gly Leu Asn Phe Ala Ala Gln Tyr Gln
145                 150                 155                 160
Gly Lys Asn Asp Arg Ser Asp Phe Asp Asn Tyr Thr Glu Gly Asn Gly
                165                 170                 175
Asp Gly Phe Gly Phe Ser Ala Thr Tyr Glu Tyr Glu Gly Phe Gly Ile
               180                 185                 190
Gly Ala Thr Tyr Ala Lys Ser Asp Arg Thr Asp Thr Gln Val Asn Ala
           195                 200                 205
Gly Lys Val Leu Pro Glu Val Phe Ala Ser Gly Lys Asn Ala Glu Val
        210                 215                 220
Trp Ala Ala Gly Leu Lys Tyr Asp Ala Asn Asn Ile Tyr Leu Ala Thr
225                 230                 235                 240
Thr Tyr Ser Glu Thr Gln Asn Met Thr Val Phe Ala Asp His Phe Val
                245                 250                 255
Ala Asn Lys Ala Gln Asn Phe Glu Ala Val Ala Gln Tyr Gln Phe Asp
               260                 265                 270
Phe Gly Leu Arg Pro Ser Val Ala Tyr Leu Gln Ser Lys Gly Lys Asp
           275                 280                 285
Leu Gly Val Trp Gly Asp Gln Asp Leu Val Lys Tyr Val Asp Val Gly
        290                 295                 300
Ala Thr Tyr Tyr Phe Asn Lys Asn Met Ser Thr Phe Val Asp Tyr Lys
305                 310                 315                 320
Ile Asn Leu Leu Asp Lys Asn Asp Phe Thr Lys Ala Leu Gly Val Ser
                325                 330                 335
Thr Asp Asp Ile Val Ala Val Gly Leu Val Tyr Gln Phe
                340                 345
```

DIAGNOSTIC METHOD AND DEVICES FOR AUTOIMMUNE DISEASE

CROSS-REFERENCE TO RELATED APPLICATIONS

This Application claims priority to U.S. Provisional Application No. 62/462,771, filed Feb. 23, 2017, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 29, 2018, is named 6219-40006US2 SL.txt and is 32,716 bytes in size.

BACKGROUND

Field

Diagnostic devices and method utilizing plasma reactivity to microbial protein to diagnosing autoimmune diseases.

Description of Art

Autoimmune disease is a group of systemic inflammatory syndromes characterized by the presence of autoantibodies. The spectrum of autoimmune disease is large, involving many different organ systems. Autoantibodies characteristic of autoimmune diseases are equally as diverse in their biochemical properties. Despite this diversity, autoantibodies share a common trait in that they target proteins of an individual's one body. Targeting an individual's own proteins, autoantibodies induce inflammation and damage symptomatic of autoimmune disease.

Crohn's disease, for instance, is a type of idiopathic inflammatory bowel disease. Diagnosing Crohn's disease often involves rather unpleasant procedures, such as colonoscopies. Rather than initially expose patients to such unpleasant procedures, Crohn's disease is other diagnosed after ruling out other possible causes for the patient's symptoms. The lack of minimally invasive test for Crohn's disease, consequently, delays diagnosis and treatment. Accordingly, less invasive diagnostic means to expedite diagnosis and treatment are needed.

Similarly, Sjogren's syndrome is a specific systemic immune disorder characterized by predominantly dry eye and dry mouth. The gold standard diagnosis for Sjogren's syndrome is a lip biopsy of the minor salivary glands, which may result in long-lasting lower lip numbness. Accordingly, less invasive diagnostic means are needed.

SUMMARY

Autoimmune diseases, such as Crohn's disease and Sjogren's syndrome, may be diagnosed without biopsies and colonoscopies by obtaining a plasma sample from an individual, quantifying antibodies levels within a plasma sample from the individual and comparing the antibody levels to a reference. The antibodies quantified may be directed against commensal microbial proteins. Commensal microbes are micro-organisms present on body surfaces, such as gastrointestinal tract, respiratory tract, vaginal, skin, etc., and exposed to the external environment. Accordingly, the antibodies quantified may be antibodies produced by the patient against proteins from commensal microbes, such as bacteria, mycobacteria and fungi. In combination or the alternative, the antibodies quantified may be autoimmune antibodies capable of reacting to, i.e. binding to, either proteins from commensal microbes and proteins from the patient. Such cross-reactivity may be improved by utilizing proteins homologous to human proteins. That is, the microbial proteins utilized may share a sufficiently similar structure, motif and/or sequence, such that autoantibodies within the serum sample against the patient's proteins can cross-react with, i.e. bind to, the microbial protein.

Quantifying antibody levels within a plasma sample reactive to proteins from commensal microbes may be accomplished by the quantifying binding between antibodies within the sample and the microbial proteins. Prior to quantifying binding, however, antibodies within the plasma sample have to be induced to bind to the microbial proteins. This may be accomplished by simply exposing a plasma sample to a microbial protein, which may or may not be homologous to a human protein. The amount of binding resulting from such an exposure that may be quantified by a label indicating the presence of binding between the microbial protein and antibodies within the sample.

For instance, binding between antibodies within a plasma sample and microbial proteins may be quantified with a diagnostic solution comprising a microbial protein homologous to a human protein, a fluorophore bound to the microbial protein, an antibody against human antibodies, and a second fluorophore bound to the antibody against antibodies. The plasma sample obtained from the individual may be added to the solution. Binding between the antibodies within the sample and microbial proteins within the solution may then be detected by energy transfer between the fluorophores. Accordingly, the fluorophores may be capable of participating in energy transfer when collectively bound to the microbial protein. The fluorophores will be collectively bound to the protein when two separate bindings occur. The first binding is of the microbial protein within the solution to antibodies within the plasma sample added to the solution. This first binding binds microbial protein to an antibody within the plasma sample. The second binding is that of the antibody against antibodies to antibodies within the plasma sample added to the solution. This second binding binds the second fluorophore to antibodies within the sample via the antibody against antibodies. When both bindings occur, the second fluorophore is bound to the first microbial protein via a linkage comprising an antibody within the sample and an antibody against antibodies from the solution. The linkage should place the first fluorophore sufficiently close to the second fluorophore that energy may be transferred from the first fluorophore to the second fluorophore.

Energy may be transferred between the fluorophores by exposing the solution to a wavelength and intensity of light sufficient to excite one of the fluorophores. When the other fluorophore is sufficiently close, energy may be transferred from the excited fluorophore to the other fluorophore, thereby causing the other fluorophore to emit light at a different wavelength than that used to stimulate the initial fluorophore. The intensity of light at the emitted wavelength may then be quantified using various devices, such as a spectrometer, to thereby quantify binding between antibodies within the sample and the microbial protein within the solution.

The solution may comprise more than one microbial protein. As to quantify binding between different microbial proteins, each microbial protein may be bound to a fluorophore emitting light of different wavelengths after being excited by energy transferred from fluorophores bound to the antibodies against antibodies.

Microbial proteins within the solution may be free floating and/or immobilized on a surface of a container holding the vessel. As to facilitate the use of light to quantify binding, the container holding the solution may be transparent to at least one wavelength of light.

Binding between antibodies within a plasma sample and microbial proteins may be quantified with a diagnostic device comprising a first surface area, a first microbial bacterial homologous to a first human protein, the first microbial protein bound to the first surface area, and a solution comprising labeled antibodies against antibodies. Quantifying binding with such a device may be accomplished by obtaining a plasma sample from an individual and exposing the plasma sample to the first microbial protein by placing the sample over the first surface area. Such exposure will induce binding between the first microbial protein bound to the first surface area and antibodies within the sample. The first surface may then be washed with a buffer or other appropriate solution that will not denature or disrupt binding between antibodies within the sample and the first microbial protein. The washed surface may then be exposed to solution of labeled antibodies against antibodies. Such exposure may comprise submerging at least a portion of the first surface area in the solution of labeled antibodies. During exposure, the labeled antibodies will bind to the antibodies that have previous bound to the first microbial proteins. The surface may then be washed again to remove unbound labeled antibodies. The amount of labeled antibodies remaining may then be quantified.

The diagnostic device may comprise a second surface area and a second microbial protein homologous to a second human protein, the second microbial protein bound to the second surface area. Additional areas with additional microbial proteins homologous to additional human proteins may also be present. Incorporating such multiple areas and microbial proteins may enable quantifying the amount of multiple antibodies within a plasma sample. When multiple microbial proteins are present, the quantified binding between the multiple microbial proteins and antibodies within the sample may be contrasted to multiple references. Each of the references may be unique to one of the multiple microbial proteins present. The reference should be indicative of binding within samples from healthy individuals.

All or a portion of the microbial proteins may be bound to their respective surface areas directly or indirectly. For instance, a capture antibody capable of binding to all or a portion of the microbial proteins may be bound to the surface, and the microbial proteins may be bound to the surface via binding to the capture antibody.

Quantifying binding may be accomplished by observing reactions of the labels on the labeled antibodies against antibodies. For example, if the label on the antibodies against antibodies participates in a chemical reaction, then the product of that reaction may be quantified to quantified binding. For instance, the label may induce a color change that can be quantified with a spectrometer. The reference in such an instance may be absorption of light of a particular wavelength. The reference may also be a color chip or color scale.

The label may luminesce, in which case binding can be quantified by measuring the intensity of light at a particular wavelength with a spectrometer. In such a case, the reference value may be an intensity value.

Binding may be quantified by observing the interaction between labels on the antibodies against antibodies and labels bound to the microbial proteins bound to the various surface areas. For example, if the label on the antibodies against antibodies comprises a fluorophore and the microbial protein bound to surface has a fluorophore bound to it, then transfer of energy between the fluorophores following exposure to light may be quantified.

When light is used to quantify binding, whether emitted, absorbed or observed color, it may be advantageous for each of the surface areas to include transparent portions.

The microbial proteins utilized within the diagnostic device, diagnostic solution and method may comprise at least a portion of at least a portion of at least one of RPOB (SEQ ID: NO. 1), EF-G (SEQ ID NO. 2), hsp65 (SEQ ID NO. 3), ATP5a (SEQ ID NO. 4) and EF-Tu (SEQ ID NO. 5), or any combination thereof. Accordingly, the whole protein may not be necessarily. When only a portion of the microbial protein is utilized, it should be a portion homologous to a portion of a human protein such that the portions share a sufficiently similar structure, motif and/or sequence, such that autoantibodies within the serum sample against the patient's proteins can cross-react with, i.e. bind to, the portion of microbial protein utilized.

As the foregoing should make evident, a method of quantifying a clinically significant amount of antibodies may comprise:
  obtaining a plasma sample from an individual;
  exposing the sample to a first microbial protein homologous to human protein;
  quantifying binding between antibodies within the sample and the first microbial protein; and
  contrasting the quantified binding to a reference.

When practicing the foregoing method, the first microbial protein may comprise at least a portion of at least one of RPOB, EF-G, hsp65 ATP5a and EF-Tu.

When any of practicing the foregoing methods, the first microbial protein may be bound to a surface, and quantifying binding comprises:
  washing the surface after exposing the sample to the first microbial protein;
  exposing the washed surface to a labeled antibody against antibodies;
  washing the surface after exposure to the labeled antibody; and
  quantifying the amount of labeled antibody remaining on the surface.

Any of the foregoing methods, may further comprise:
  exposing the first microbial protein to a labeled antibody against the first microbial protein, wherein the labeled antibody against the first microbial protein comprises a first fluorophore; and
  exposing the first microbial protein exposed to the plasma sample to a labeled antibody against antibodies, the labeled antibody against antibodies comprising a second fluorophore capable of participating in an energy transfer with the first fluorophore the labeled antibody against the first microbial protein and the labeled antibody against antibodies are collectively bound to the first microbial protein, and
  wherein quantifying binding comprises quantifying energy transfer between first and second fluorophore.

Any of the foregoing methods, may further comprise:
  exposing the sample to a second microbial protein homologous to a second human protein, the second microbial protein different than the first microbial protein and comprising at least a portion of at least one of RPOB, EF-G, hsp65 ATP5a and EF-Tu;

quantifying binding between antibodies within the sample and the second microbial protein; and contrasting the quantified binding between the antibodies and the second microbial protein to a second threshold value.

As the foregoing should make evident, a diagnostic solution may comprise:
 a microbial protein homologous to a human protein;
 a first fluorophore bound to the microbial protein;
 an antibody against antibodies;
 a second fluorophore bound to the antibody against antibodies.

Within the diagnostic solution, the microbial protein may comprise at least a portion of at least one of RPOB, EF-G, hsp65 ATP5a and EF-Tu, or any combinations thereof.

Within any of the foregoing diagnostic solutions, the first fluorophore and second fluorophore may be capable of participating in an energy transfer when collectively bound to the microbial protein.

Any of the foregoing diagnostic solutions may further comprise a serum sample from an individual.

In any of the foregoing diagnostic solutions, the microbial protein may be immobilized on a surface of a container holding the solution.

As the foregoing should make evident, a diagnostic device may comprise:
 a first surface area;
 a first microbial protein homologous to a first human protein, the first microbial protein bound to the first surface area;
 a solution comprising labeled antibodies against antibodies.

Within the diagnostic device may the first microbial protein bound to the first surface area may comprise at least a portion of at least one of RPOB, EF-G, hsp65 ATP5a and EF-Tu or any combination thereof.

Any of the foregoing diagnostic devices may further comprise:
 a second surface area; and
 a second microbial protein homologous to a second human protein, the second microbial protein bound to the second surface area.

Within any of the foregoing diagnostic devices, a second microbial protein bound to the second surface may comprise at least a portion of at least one of RPOB, EF-G, hsp65 ATP5a and EF-Tu, or any combination thereof.

Within any of the foregoing diagnostic devices, a second microbial protein and first microbial proteins may be different.

Within any of the foregoing diagnostic devices, a first surface area may comprise a transparent portion.

Within any of the foregoing diagnostic devices, a second surface area may comprise a transparent portion.

Any of the foregoing diagnostic devices may further comprise a plasma antibody bound to the first microbial protein.

Within any of the foregoing diagnostic devices, at least a portion of a first surface area may be submerged in a solution comprising labeled antibodies.

Any of the foregoing diagnostic devices may further comprise a capture antibody against the first microbial protein bound to the first surface, and wherein the first microbial protein is bound to the first surface by the capture antibody.

BRIEF DESCRIPTIONS OF THE FIGURES

Representative embodiments are disclosed in more detail with reference to the following figures, within which like elements are equivalently numbered.

Figure 1:
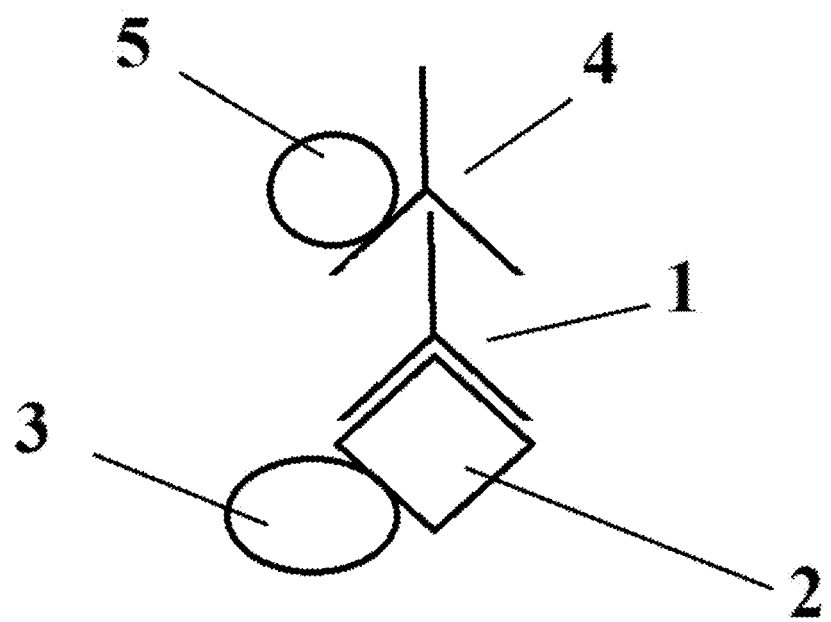
FIG. 1 depicts a binding between a labeled antibody against antibodies, a labeled microbial protein and an antibody from a plasma sample within a diagnostic solution.

FIGS. 6 and 7 show sequences of aspects described herein in accordance with aspects of the invention. FIG. 6 discloses SEQ ID NOS 1-2, respectively, in order of appearance. FIG. 7 discloses SEQ ID NOS 3-6, respectively, in order of appearance.

DETAILED DESCRIPTION

Potential exemplary embodiments now will be described more fully hereinafter with reference to the accompanying drawings, which form a part hereof. The presented exemplary embodiments, however, should not be construed as limiting the scope of this disclosure of the accompanying claims. Rather, these embodiments are provided so that this disclosure will be thorough and complete, and will fully convey the scope of the accompanying claims to those skilled in the art.

It should be noted that although the discussions herein may refer to a specific order and composition of method steps, it is understood that the order of these steps may differ from what is described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of this disclosure and the accompanying claims.

Throughout the specification and claims, the following terms take the meanings explicitly associated herein, unless the context clearly dictates otherwise. The phrase "in one embodiment" or "in some embodiments" or "in a preferred embodiment" as used herein does not necessarily refer to the same embodiment, though it may. Furthermore, the phrase "in another embodiment" as used herein does not necessarily refer to a different embodiment, although it may. Thus, as described below, various embodiments may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Autoimmune diseases, such as Crohn's disease and Sjogren's syndrome, may by diagnosed without biopsies and colonoscopies by obtaining a plasma sample from an individual, quantifying antibodies levels within a plasma sample from the individual and comparing the antibody levels to a reference indicative of antibodies levels within individuals without an autoimmune disease. The antibodies quantified may be directed against commensal microbial proteins. Accordingly, the antibodies quantified may be antibodies produced by the patient against proteins from commensal microbes. In combination or the alternative, the antibodies quantified may be autoimmune antibodies capable of reacting to either proteins from commensal microbes and proteins from the patient. Such cross-reactivity may be improved by utilizing proteins homologous to human proteins.

Quantifying antibody levels within a plasma sample reactive to proteins from commensal microbes may be accomplished by the quantifying binding between antibodies within the sample and the microbial proteins. Prior to quantifying binding, however, antibodies within the plasma sample have to be induced to bind to the microbial proteins. This may be accomplished by simply exposing a plasma sample to a microbial protein, which may or may not be homologous to a human protein. The amount of binding resulting from such an exposure than may be quantified by a label indicating the presence of binding between the microbial protein and antibodies within the sample.

As shown in FIG. 1, binding between antibodies 1 within a plasma sample and microbial proteins 2 may be quantified with a diagnostic solution comprising a microbial protein 2 homologous to a human protein, a fluorophore 3 bound to the microbial protein 2, an antibody 4 against human antibodies, and a second fluorophore 5 bound to the antibody 4 against antibodies. The plasma sample obtained from the individual may be added to the solution. Binding between the antibodies 1 within the sample and microbial proteins 2 within the solution may then be detected by energy transfer between the fluorophores. Accordingly, fluorophores 3 and 5 may be capable of participating in energy transfer when collectively bound to microbial protein 2. Fluorophores 3 and 5 will be collectively bound to protein 2 when two separate bindings occur. The first binding is of microbial protein 2 within the solution to an antibody 1 within the plasma sample added to the solution. This first binding binds microbial protein 2 to antibody 1. The second binding is that of antibody 4 against antibodies to an antibody 1 within the plasma sample added to the solution. This second binding binds second fluorophore 5 to an antibody 1 within the sample via the antibody 4 against antibodies. When both bindings occur, second fluorophore 5 is bound to microbial protein 2 via a linkage comprising antibody 1 within the sample and antibody 4 against antibodies from the solution. The linkage should place fluorophore 3 sufficiently close to second fluorophore 5 that energy may be transferred from fluorophore 3 to fluorophore 5 when stimulated with light.

Energy may be transferred between fluorophores 3 and 5 by exposing the solution to a wavelength and intensity of light sufficient to excite one of fluorophores 3 and 5. When sufficiently close, energy may be transferred from the excited fluorophore to the other fluorophore, thereby causing the other fluorophore to emit light at a different wavelength than that used to stimulate the initial fluorophore. The intensity of light at the emitted wavelength may then be quantified using various devices, such as a spectrometer, to thereby quantify binding between antibody 1 within the sample and microbial protein 2 within the solution.

The solution may comprise more than one microbial protein. As to quantify binding between different microbial proteins, each microbial protein may be bound to a fluorophore emitting light of different wavelengths after being excited by energy transferred from fluorophores bound to the antibodies against antibodies.

Microbial proteins within the solution may be free floating and/or immobilized on a surface of a container holding the vessel. As to facilitate the use of light to quantify binding, the container holding the solution may be transparent to at least one wavelength of light.

Figure 2:
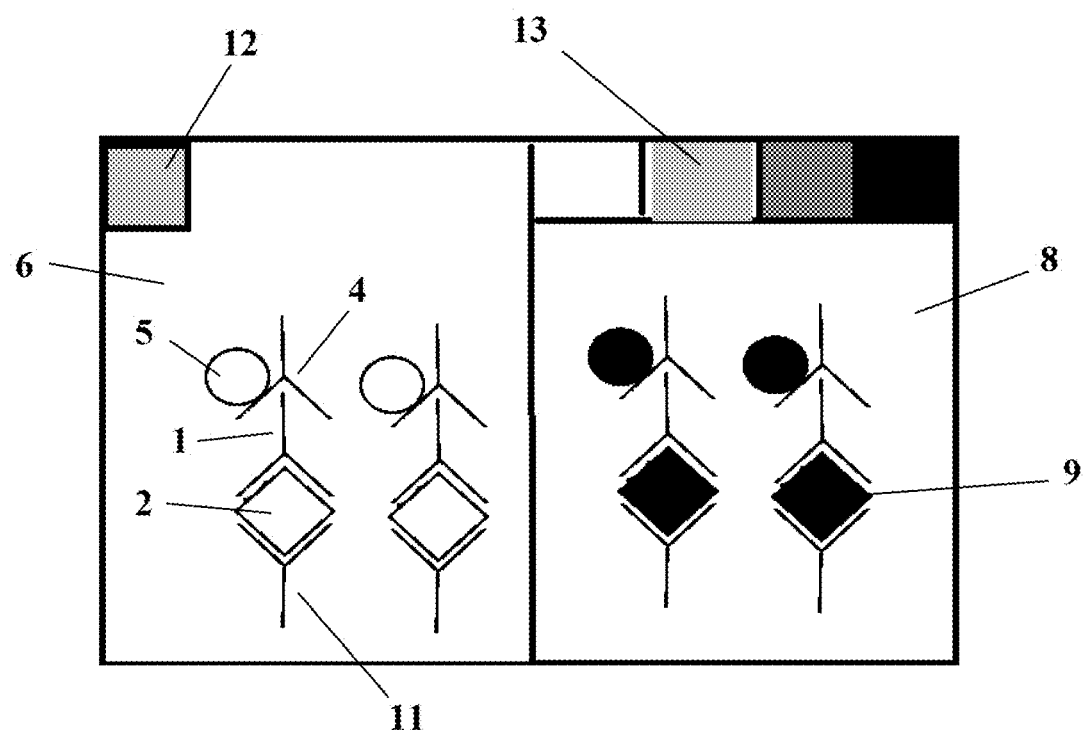
FIG. 2 depicts a diagnostic device having a first and second surface.

As shown in FIG. 2, binding between antibodies 1 within a plasma sample and microbial proteins 2 may be quantified with a diagnostic device comprising a first surface area 6, a first microbial bacterial 2 homologous to a first human protein, the first microbial protein bound to the first surface area 6, and a solution comprising labeled antibodies 4 against antibodies. Quantifying binding with such a device may be accomplished by obtaining a plasma sample from an individual and exposing the plasma sample to first microbial protein 2 by placing the sample over first surface area 6. Such exposure will induce binding between first microbial protein 2 bound to first surface area 6 and antibodies 1 within the sample. First surface 6 may then be washed with a buffer or other appropriate solution that will not denature or disrupt binding between antibodies 1 within the sample and first microbial proteins 2. Washed surface area 6 may then be exposed to solution of labeled antibodies 4 against antibodies. Such exposure may comprise submerging at least a portion of first surface area 6 in the solution of labeled antibodies. When first surface area 6 comprises surfaces of a well 7, as shown in in FIG. 3, submerging first surface 6 may be accomplished by filling a portion of well 7 with a solution comprising labeled antibodies 4 against antibodies. During exposure, labeled antibodies 4 will bind to antibodies 1 that have previous bound to first microbial proteins 2. Surface area 6 may then be washed again to remove unbound labeled antibodies 4. The amount of labeled antibodies 4 remaining may then be quantified.

Figure 3:
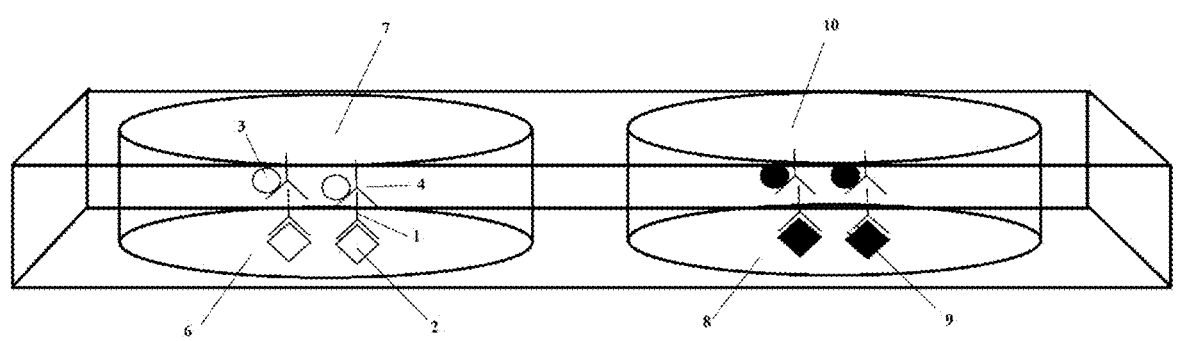
FIG. 3 depicts a diagnostic device having a first surface within a first well and a second surface with a second well.

The diagnostic device may comprise a second surface area 8 and a second microbial protein 9 homologous to a second human protein, second microbial protein 9 bound to the second surface area. Additional areas with additional microbial proteins homologous to additional human proteins may also be present. Second surface 8 may be a separate region on a surface common to surface area 6 and 8, as shown in FIG. 2. Second surface area 8 may comprise a surface of a distinct well 10, as shown in FIG. 3. Incorporating such multiple areas and microbial proteins may enable quantifying the amount of multiple antibodies within a plasma sample. When multiple microbial proteins are present, the quantified binding between the multiple microbial proteins and antibodies within the sample may be contrasted to multiple references. Each of the references may be unique to one of the multiple microbial proteins present. The reference should be indicative of binding within samples from healthy individuals.

All or a portion of the microbial proteins may be bound to their respective surface areas directly, as shown in FIG. 3, or indirectly, as shown in FIG. 2. As shown in FIG. 2, indirect binding may be facilitated by a capture antibody 11 bound to surface area 6 that is capable of binding to all or a portion of microbial proteins 2, such that microbial proteins 2 are bound to surface area 6 via binding to the capture antibody 11.

Quantifying binding may be accomplished by observing reactions of labels 3 on the labeled antibodies 4 against antibodies. For example, if label 3 on the antibodies 4 against antibodies participates in a chemical reaction, then the product of that reaction may be quantified to quantified binding. For instance, label 3 comprises an enzyme, such as horseradish peroxidase, capable of inducing a color change that can be quantified with a spectrometer. The reference in such an instance may be absorption of light of a particular wavelength. The reference may also be a color chip 12 and/or color scale 13. As shown in FIG. 2, color chip 12 and/or color scale 13 may be attached and/or printed on surface areas 6 and 8. Color scale 13 and/or color chip 12 may also be detached from surface 6 and/or 8. For instance, color scale 13 and/or color chip 12 may printed on card.

Label 3 may luminesce, in which case binding can be quantified by measuring the intensity of light at a particular wavelength with a spectrometer. In such a case, the reference value may be an intensity value.

Binding may be quantified by observing the interaction between labels on the antibodies against antibodies and labels bound to the microbial proteins bound to the various surface areas. For example, if label 3 on antibodies 4 against antibodies comprises a fluorophore and the microbial protein 2 bound to surface has a fluorophore bound to it, then transfer of energy between the fluorophores following exposure to light may be quantified.

When light is used to quantify binding, whether emitted, absorbed or observed color, it may be advantageous surface area 6 and/or surface area 8 to include transparent portions.

The microbial proteins utilized within the diagnostic device, diagnostic solution and method may comprise at least a portion of at least a portion of at least one of RPOB (SEQ ID: NO. 1), EF-G (SEQ ID NO. 2), hsp65 (SEQ ID NO. 3), ATP5a (SEQ ID NO. 4) and EF-Tu (SEQ ID NO. 5), or any combination thereof, sequences of which are shown in FIGS. 6 and 7. Accordingly, the whole protein may not be necessarily. When only a portion of the microbial protein is utilized, it should be a portion homologous to a portion of a human protein such that the portions share a sufficiently similar structure, motif and/or sequence, such that autoantibodies within the serum sample against the patient's proteins can cross-react with, i.e. bind to, the portion of microbial protein utilized.

DNA-directed RNA polymerase subunit B (RPOB) is a microbial protein from *Staphylococcus aureus* critical for gene transcription. It is also a clinically relevant target for antibiotic rifampin, one of the most important drug for tuberculosis. Mutation of RPOB gene confers rifampin resistance in *Escherichia Coli, S. aureus* and *Mycobacterium tuberculosis*. There is less than 50% homology between the RPOB of *S. aureus* and that of the human counterpart.

Elongation factor G (EF-G) is a microbial protein from *S. pseudintermedius*, which has a potential to be pathogenic in humans. EF-G is a critical regulator for bacterial protein translation and protein synthesis, and it is present in all bacteria species. Human counterpart of the bacterial EF-G is present in the mitochondria (G elongation factor mitochondrial 1, GFM1), and it plays similar roles in human protein biosynthesis. The homology between the bacterial protein and the human protein at the amino acid levels is 61%.

Heat shock protein 65 (hsp65) is a protein from *Mycobacterium avium* subspecies *paratuberculosis* homologous to human hsp60. Hsp60 is known to be an autoantigen with elevated antibody levels in cancer patients and other autoimmune diseases.

ATP synthase alpha (ATP5a) is a microbial protein from *S. aureus* and *S. pseudintermedius* The homologous human protein is present in the mitochondria and plays a significant role in generation of the cellular energy source ATP.

Elongation factor Tu (EF-Tu) is a microbial protein from *E. coli* homologous to human EF-Tu mitochondrial precursor. There is no known disease associated with this protein.

Figure 4:
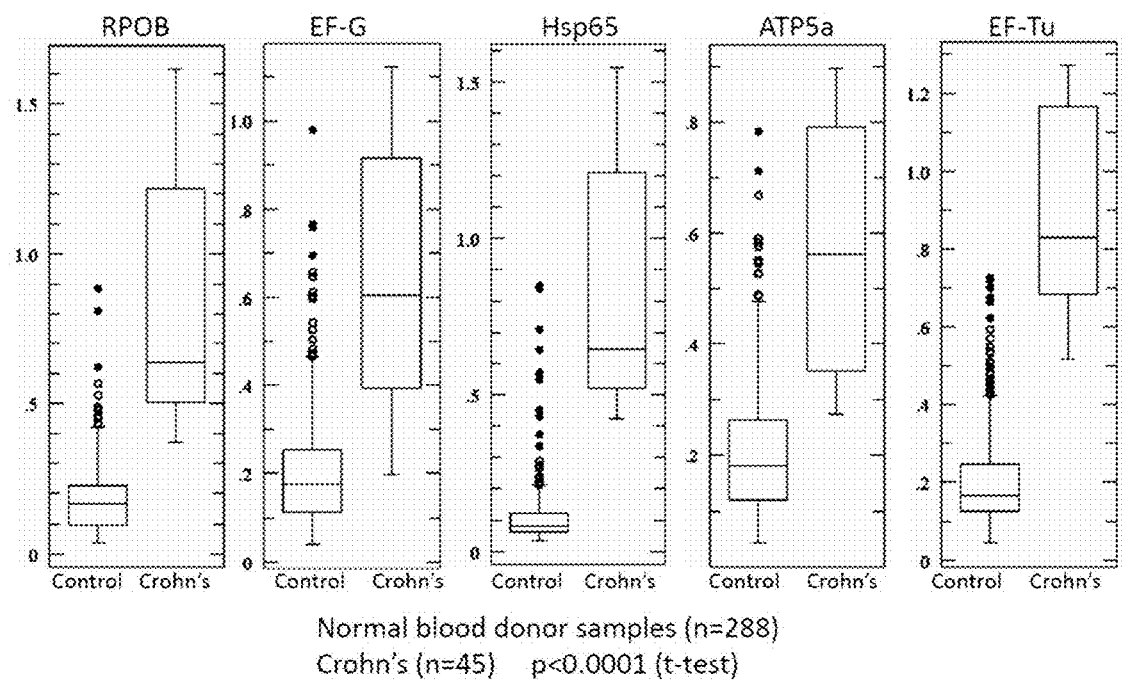
FIG. 4 shows a comparison between plasma levels for antibodies against microbial proteins in individual without autoimmune disease and individuals with Crohn's disease.

FIG. 4 shows antibody levels against microbial proteins RPOB, EF-G, Hsp65, ATP5a and EF-Tu in individual without autoimmune disease and those with Crohn's disease. From a Red Cross Blood center, 288 blood samples were screened for the presence of anti-microbial antibodies. Typically, the segment of the red blood cell donor unit contains 0.5 ml red blood cells in the storage buffer. The unit segments were cut open and washed with 1 ml normal saline into the Eppendorf tubes. The cellular components were collected at the bottom of the Eppendorf tube after centrifugation at 15,000 g for 1 minute. The supernatants were collected to fresh Eppendorf tubes and 100 microliter of the supernatants were used for our panel assays. The prevalence antibodies against the microbial proteins blood samples is:

RPOB—4 out of 288 (1.40%)
EF-G—11 out of 288 (3.86%)
Hsp65—4 out of 288 (1.40%)
ATP5a—13 out of 288 (4.56%)
EF-Tu—13 out of 288 (4.56%)

As shown in FIG. 4, the antibodies levels against the above microbial proteins are significantly elevated in individuals with Crohn's disease.

Figure 5:
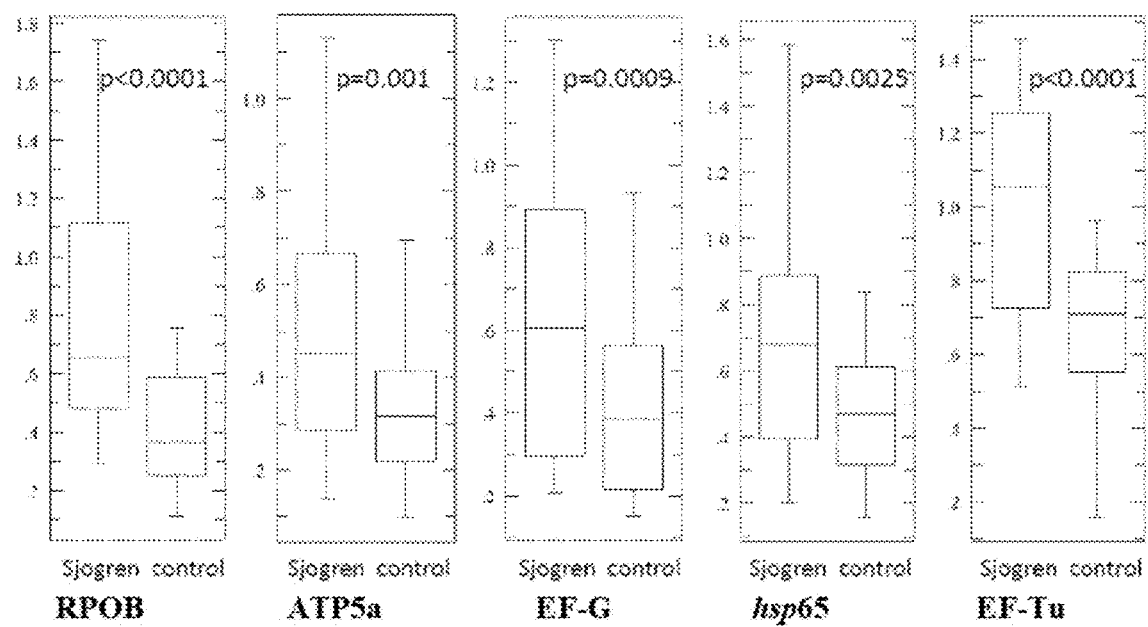
FIG. 5 shows preliminary validation of individuals with Sjogren's syndrome.

As shown in FIG. 5, antibodies levels against the above microbial proteins are also elevated in individuals with Sjorgen's syndrome. Plasma samples from 23 patients were analyzed of which: 19 patients were positive for one or more markers (83%; 6 patients positive for all markers, 4 patients positive for 4 markers, 4 patients positive for 3 markers, 4 patients positive for 2 markers, 1 positive for 1 marker), and 4 patients were negative for all markers (17%). These plasma samples were matched against samples from healthy volunteers.

While exemplary embodiments have been presented, it will become apparent to one of ordinary skill in the art that many modifications, improvements and sub-combinations of the various embodiments, adaptations and variations can be made without departing from the spirit and scope of this disclosure and accompanying claims.

The invention claimed is:

1. A diagnostic device comprising:
a first surface area having a first bacterial protein homologous to a first human protein bound thereto;
a second surface area having a second bacterial protein homologous to a second human protein bound thereto and
a solution comprising labeled antibodies against antibodies to the first bacterial protein and antibodies to the second bacterial protein,
wherein the second bacterial protein is different from the first bacterial protein and wherein the first bacterial protein and the second bacterial protein are selected from the group consisting of RNA polymerase B (PROB), elongation factor G (EF-G), heat shock protein 65 (hsp65), ATP synthase alpha (ATP5a), and elongation factor Tu (EF-Tu).

2. The diagnostic device of claim 1, wherein the first surface area comprises a transparent area.

3. The diagnostic device of claim 1, wherein the second surface area comprises a transparent area.

4. The diagnostic device of claim 3, wherein at least a portion of the first surface area is submerged in the solution comprising the labeled antibodies.

5. The diagnostic device of claim 1, further comprising a capture antibody against the first bacterial protein and wherein the first bacterial protein is bound to the first surface area by the capture antibody.

6. The diagnostic device of claim 1, further comprising a capture antibody against the second bacterial protein and wherein the second bacterial protein is bound to the second surface area by the capture antibody.

* * * * *